United States Patent [19]

Rosenberger

[11] 4,322,303
[45] Mar. 30, 1982

[54] DITHIOPHOSPHATE STABILIZERS

[75] Inventor: Siegfried Rosenberger, Riehen, Switzerland

[73] Assignee: Ciba-Geigy Corporation, Ardsley, N.Y.

[21] Appl. No.: 185,841

[22] Filed: Sep. 10, 1980

[30] Foreign Application Priority Data

Sep. 18, 1979 [CH] Switzerland ............... 8417/79

[51] Int. Cl.³ ............... C08K 5/51; C07C 161/00
[52] U.S. Cl. ............... 252/46.6; 260/455 P; 260/926; 260/927 R; 260/941; 260/942; 260/943; 260/929; 524/137; 524/122
[58] Field of Search ............... 260/45.85 B, 45.8 R, 260/45.9 NC, 455 P, 926, 927, 937, 941, 942, 943, 45.95 C, 929; 252/49.8, 49.9, 46.6

[56] References Cited

U.S. PATENT DOCUMENTS

| | | | |
|---|---|---|---|
| 2,875,228 | 2/1959 | Birum | 260/455 P |
| 3,017,422 | 1/1962 | Thompson | 260/461 |
| 3,112,338 | 11/1963 | Smutny et al. | 260/45.85 B |
| 3,285,855 | 11/1966 | Dexter et al. | 260/45.85 B |
| 3,326,943 | 6/1967 | Greenbaum | 260/455 P |
| 3,350,348 | 10/1967 | Braid | 252/46.6 |
| 3,567,638 | 3/1971 | Braid | 252/46.6 |
| 3,639,538 | 1/1972 | Kleiner | 260/941 |
| 3,708,520 | 1/1973 | Dexter et al. | 560/75 |
| 3,745,148 | 7/1973 | Shin et al. | 260/45.9 |
| 3,808,296 | 4/1974 | Brunetti | 260/927 R |
| 3,838,100 | 9/1974 | Eggensperger et al. | 260/45.95 C |
| 3,873,498 | 3/1975 | Brunetti | 260/45.95 D |
| 4,081,387 | 3/1978 | Ripple | 252/46.6 |
| 4,101,432 | 7/1978 | Okorodudu | 252/49.8 |

FOREIGN PATENT DOCUMENTS

2509654 1/1976 Fed. Rep. of Germany.

OTHER PUBLICATIONS

CA 84, 136673p (1976).
CA 91, 124371v (1979).
CA 91, 108838x (1979).
CA 91, Chemical Formula Index $C_{19}H_{28}O_3$, p. 1614f (1979).
Aldrich Chemical Co. 1979–1980 catalog, pp. 30, 31, 567 and 659.
CA 77, 6964d 1972.

*Primary Examiner*—V. P. Hoke
*Attorney, Agent, or Firm*—Luther A. R. Hall

[57] ABSTRACT

Compounds of the formula

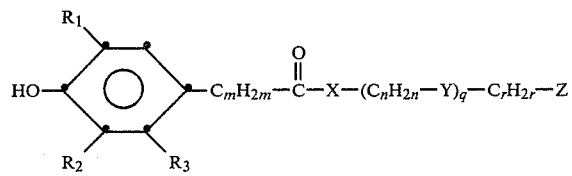

wherein the symbols $R_1$, $R_2$, $R_3$, m, X, n, Y, q, r and Z have the meanings given in Claim 1. The divalent radical Y can optionally contain a group of the formula

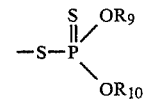

wherein $R_9$ and $R_{10}$ have the meanings given in Claim 1. The compounds according to the invention are suitable as antioxidant-stabilizers in organic materials, and impart to lubricants, in addition to having therein a good anti-oxidation and anti-corrosion action, excellent extreme pressure and antiwear properties.

12 Claims, No Drawings

DITHIOPHOSPHATE STABILIZERS

The present invention relates to novel phenols, to their use as stabilisers for organic material, particularly for lubricants, to the production of the novel compounds, and to the organic material stabilised therewith.

Antioxidant-stabilisers containing phenol groups for stabilising organic material, especially polymers, are known. For the U.S. Pat. Nos. 3,745,148 and 3,017,422 is also known the use of stabilisers containing phenol and dithiophosphate groups for stabilising lubricants. The described compounds however do not satisfy, or at most only partly satisfy, the high requirements which a high-pressure and antiwear additive has to meet.

There has now been found a new class of phenol-containing compounds which produce in organic materials a high colour- and extraction-stability, and impart to lubricants, in addition to having therein a good anti-oxidation and anti-corrosion action, excellent extreme pressure and antiwear properties. Furthermore, the novel compounds in lubricants are characterised by negligible formation of sediment and by no formation of ash.

The novel compounds correspond to the general formula I $$\text{HO} - \underset{R_2}{\underset{|}{\overset{R_1}{\overset{|}{\bigcirc}}}} - C_mH_{2m} - \overset{O}{\overset{\|}{C}} - X - (C_nH_{2n} - Y)_q - C_rH_{2r} - Z \quad (I)$$

wherein $R_1$ and $R_2$ independently of one another are each $C_1$–$C_{12}$-alkyl, or they are phenyl, $C_7$–$C_9$-aralkyl or $C_5$–$C_7$-cycloalkyl, each of which is unsubstituted or substituted by 1 to 3 alkyl groups having a total of 1 to 12 C atoms, and $R_2$ in addition is hydrogen or chlorine, $R_3$ is hydrogen or methyl, m is nought, 1, 2, 3 or 4, X is —O—, —S— or —NH—, n and r independently of one another are each an integer from nought to 20 inclusive, q is 1, 2 or 3, with the proviso that $(n \cdot q) + r$ is an integer from nought to 24 inclusive, and Y is a group of the formula II or III $$-\overset{}{\underset{R_4}{\overset{R_6}{\overset{|}{C}}}}-\overset{}{\underset{R_5}{\overset{|}{C}}}- \quad (II), \quad -\overset{}{\underset{R_7}{\overset{|}{C}}}=\overset{}{\underset{R_8}{\overset{|}{C}}}- \quad (III)$$

in which $R_4$ and $R_5$ are each hydrogen or hydroxyl, and at least one of the radicals $R_4$ and $R_5$ is a group of the formula IV $$-S-\overset{S}{\overset{\|}{P}}\diagup\overset{OR_9}{\diagdown OR_{10}} \quad (IV)$$

$R_6$ is hydrogen or methyl, $R_7$ and $R_8$ are both hydrogen, or together they form a further C—C bond, n at the same time being 1, or one of the radicals $R_7$ and $R_8$ is hydrogen, and the other is a group of the formula IV, wherein $R_9$ and $R_{10}$ independently of one another are each $C_1$–$C_{30}$-alkyl or $C_2$–$C_{10}$-alkoxyalkyl, or they are phenyl, $C_7$–$C_9$-aralkyl or $C_5$–$C_7$-cycloalkyl, each of which is unsubstituted or substituted by 1 to 3 alkyl groups having a total of 1 to 12 C atoms, or $R_9$ and $R_{10}$ together are a group of the formula V $$-(R_{11})C(R_{12})-[(R_{13})C(R_{14})]_t-(R_{15})C(R_{16})- \quad (V)$$

wherein t is nought or 1, and $R_{11}$, $R_{12}$, $R_{13}$, $R_{14}$, $R_{15}$ and $R_{16}$ independently of one another are each hydrogen or methyl, and Z is hydrogen or a group of the formula VI $$-X-\overset{O}{\overset{\|}{C}}-C_mH_{2m}-\underset{R_3}{\underset{|}{\overset{R_1}{\overset{|}{\bigcirc}}}}-OH, \quad (VI)$$

in which the symbols $R_1$, $R_2$, $R_3$, m and X have the meanings defined above.

$R_1$ and $R_2$ as $C_1$–$C_{12}$-alkyl are for example: methyl, ethyl, iso-propyl, sec-butyl, t-butyl, t-amyl, n-hexyl, 1,1,3,3-tetramethylbutyl or 1,1,3,3,5,5-hexamethylhexyl. Preferred alkyl groups having 1 to 8 C atoms. In preferred compounds, $R_1$ is t-butyl, t-amyl or 1,1,3,3-tetramethylbutyl.

When $R_1$, $R_2$, $R_9$ and $R_{10}$ are $C_7$–$C_9$-aralkyl, this can be benzyl, α-phenylethyl or α,α-dimethylbenzyl.

If $R_1$, $R_2$, $R_9$ and $R_{10}$ are $C_5$–$C_7$-cycloalkyl, this is cyclopentyl, cyclohexyl or cycloheptyl.

$R_1$, $R_2$, $R_9$ and $R_{10}$ as phenyl, aralkyl and cycloalkyl can each be substituted by 1 to 3 alkyl groups having a total of 1 to 12 C atoms. Examples of alkyl substituents of this type are: methyl, ethyl, isopropyl, n-butyl, sec-butyl, t-butyl, n-hexyl, 1,1,3,3-tetramethylbutyl, n-nonyl, 1,1,3,3,5,5-hexamethylhexyl or n-dodecyl.

The preferred meaning of $R_3$ is hydrogen, of m it is 1 or 2, and of X it is —O—.

The group $-C_mH_{2m}$ can be a branched-chain alkylene group, but preferably it is a straight-chain alkylene group.

Independently of one another, n and r can be an integer from nought to 20 but preferably from nought to 8 inclusive. In preferred compounds, n is nought to 6 inclusive, particularly 1, and r is preferably 1 and particularly preferably it is nought.

The groups $-C_nH_{2n}-$ and $-C_rH_{2r}-$ can be straight-chain or branched-chain alkyl groups. Examples of such groups are: methylene, ethylene-1,2, propylene-1,3, butylene-1,4, pentamethylene-1,5, hexamethylene-1,6, octamethylene-1,8, nonamethylene-1,9, 1-propylidene, isopropylidene, 1-methylethylene-1,2, 1-ethylidene, 1-butylidene, 2-butylidene, 2-pentylidene, 1-pentylidene, 1-hexylidene, 3-methylpentamethylene-1,5 and 4,8,12-trimethyl-tridecamethylene-1,13.

q can be 1, 2 or 3, with the preferred meaning being 1. If q is 2 or 3, the 2 or 3 units of the formula $-(C_nH_{2n}-Y)-$ do not have to be identical. Examples of bridge members of the formula $-(C_nH_{2n}-Y)_q-$ are $-Y-CH_2-Y-$, $-CH_2-Y-Y-$, $-(CH_2)_8-Y-CH_2-Y-$ and $-(CH_2)_8-Y-CH_2-Y-CH_2-Y-$.

The compounds according to the invention satisfy the condition that the sum of $(n \cdot q) + r$ is a number from nought to 24, preferably nought to 16, and particularly nought to 6.

A preferred meaning of Y is the group of the formula II. In this formula, at least one of the radicals $R_4$ and $R_5$ has to be a group of the formula IV, the other hydroxyl or preferably hydrogen. The invention relates however also to compounds in which both $R_4$ and $R_5$ are a group of the formula IV, wherein the substituents $R_9$ and $R_{10}$ occurring in both groups preferably have the same meaning. A further preferred meaning of Y is the group of the formula III wherein $R_7$ and $R_8$ are both hydrogen, or together form a further C—C bond, n being at the same time 1.

The preferred meaning of $R_6$ is hydrogen.

Where $R_9$ and $R_{10}$ are each $C_1$–$C_{30}$-alkyl, they can be for example: methyl, ethyl, n-propyl, isopropyl, n-butyl, sec-butyl, t-butyl, n-hexyl, n-octyl, 2-ethylhexyl, 6-methylheptyl, n-octyl or straight-chain or branched-chain nonyl, decyl, dodecyl, tridecyl, tetradecyl, octadecyl, eicosyl, docosyl, tetracosyl or triacontyl. Long-chain alkyl groups consist in general of isomeric mixtures.

If $R_9$ and $R_{10}$ are $C_2$–$C_{10}$-alkoxyalkyl, the alkyl moiety can contain 1 to 3 C atoms and the alkoxy moiety 1–8 C atoms, such as in methoxymethyl, ethoxymethyl, 2-methoxyethyl, 2-ethoxyethyl, 2-n-butoxyethyl, 3-n-butoxypropyl, 2-octoxyethyl or methoxypropyl.

When $R_9$ and $R_{10}$ together are an alkylene group of the formula V, it is for example: ethylene-1,2, 1-methylethylene-1,2, 1,1-dimethylethylene-1,2, 1,1,2-trimethylethylene-1,2, 1,1,2,2-tetramethylethylene-1,2, propylene-1,3, 1-methylpropylene-1,3, 1,1,3-trimethylpropylene-1,3 or 2,2-dimethylpropylene-1,3.

The preferred meaning of Z is hydrogen.

Preferred compounds correspond to the formula I wherein $R_1$ and $R_2$ independently of one another are each $C_1$–$C_8$-alkyl, with $R_2$ in addition being hydrogen, $R_3$ is hydrogen or methyl, m is 1 or 2, X is —O—, n and r independently of one another are each an integer from nought to 8 inclusive, q is 1, with the proviso that (n·q)+r is an integer from nought to 16 inclusive, Y is a group of the formula II or III wherein $R_4$ and $R_5$ are each hydrogen or hydroxyl, and at least one of the radicals $R_4$ and $R_5$ is a group of the formula IV, $R_6$ is hydrogen, $R_7$ and $R_8$ are both hydrogen, or together form a further C—C bond, n at the same time being 1, or one of the radicals $R_7$ and $R_8$ is hydrogen, and the other is a group of the formula IV, wherein $R_9$ and $R_{10}$ independently of one another are each $C_1$–$C_{22}$-alkyl, or $R_9$ and $R_{10}$ together are a group of the formula V, wherein the symbols t and $R_{11}$ to $R_{16}$ have the meanings defined in the foregoing, and Z is hydrogen.

Of particular interest also are compounds of the formula I wherein $R_1$ is t-butyl, t-amyl or 1,1,3,3-tetramethylbutyl, $R_2$ is $C_1$–$C_8$-alkyl, $R_3$ is hydrogen, m is 1 or 2, X is —O—, n is an integer from nought to 6 inclusive, r is nought or 1, q is 1, Y is a group of the formula II or III, in which one of the substituents $R_4$ and $R_5$ is hydrogen and the other is a group of the formula IV, wherein $R_9$ and $R_{10}$ have the meanings defined in the foregoing, and $R_7$ and $R_8$ are both hydrogen, n being at the same time 1.

Examples of compounds of the formula I are summarised in the following Table. The notation "+" in the Table and in working Examples 1–4 relates to the group "tert-butyl"; and the notation "++" in the Table relates to the group "tert-octyl or 1,1,3,3-tetramethylbutyl".

Typical examples of compounds according to the invention corresponding to formula VII or VIII:

Typical examples of compounds according to the invention corresponding to formula VII or VIII:

$$A-C_mH_{2m}-\overset{O}{\underset{\|}{C}}-X-C_nH_{2n}-\overset{R_4}{\underset{|}{C}H}-\overset{R_5}{\underset{|}{C}}(R_6)-C_rH_{2r}-Z \quad (VII)$$

| No. | A | m $-C_mH_{2m}-$ | X | n $-C_nH_{2n}-$ | one of $R_4$ and $R_5$ is | and the other is | $R_6$ | r $-C_rH_{2r}-$ | Z |
|---|---|---|---|---|---|---|---|---|---|
| 1. | ![HO-phenol with t-Bu groups] | 0 | | -S- | 0 | | $-S-P(S)(O-i-C_{13}H_{27})_2$ | H | 0 | H |
| 2. | " | 3 | $-CH_2-C(CH_3)_2-CH_3-$ | -O- | 1 | $-CH_2-$ | H | ![5-membered P cycle S=P(O-)(O-)-S-] | H | 0 | H |
| 3. | " | 2 | $-CH(CH_3)-$ | -NH- | 2 | $-CH_2CH_2-$ | -OH | $-S-P(S)(O-i-C_3H_7)_2$ | H | 0 | H |
| 4. | " | 2 | $-CH_2CH_2-$ | 3 | $-(CH_2)_3-$ | H | $-S-P(S)(O-C_{22}H_{45})_2$ | H | 0 | H |
| 5. | " | 1 | $-CH_2-$ | -O- | 3 | $-CH(CH_3)CH_2-$ | H | $-S-P(S)(O-i-C_8H_{17})_2$ | H | 0 | H |
| 6. | " | 2 | $-CH_2CH_2-$ | -O- | 2 | $-CH(CH_3)-$ | H | $-S-P(S)(O-i-C_4H_9)_2$ | H | 1 | $-CH_2-$ |
| 7. | " | 1 | $-CH_2-$ | -O- | 4 | $-CH-CH_2CH_2CH_3$ | H | (cyclic phosphorodithioate) | H | 1 | $-CH_2-$ |
| 8. | " | 4 | $-(CH_2)_4-$ | -O- | 4 | $-(CH_2)_4-$ | -OH | $-S-P(S)(OC_{12}H_{25})_2$ | H | 0 | $-CH_2-$ |
| 9. | " | 2 | $-CH_2CH_2-$ | -O- | 6 | $-CH_2CH_2CH-CH_2-CH_2-CH_3$ | H | (cyclic 5,5-dimethyl phosphorodithioate) | $CH_3$ | 1 | $-CH_2-$ |
| 10. | " | 2 | $-CH_2CH_2-$ | -O- | 8 | $-(CH_2)_8-$ | H | $-S-P(S)(O-i-C_{13}H_{27})_2$ | H | 8 | $-(CH_2)_8-$ |
| 11. | " | 2 | $-CH_2CH_2-$ | -O- | 1 | $-CH_2-$ | $-S-P(S)(O-1-C_3H_7)_2$ | $-S-P(S)(O-i-C_3H_7)_2$ | H | 1 | $-CH_2-$ |
| 12. | " | 1 | $-CH_2-$ | -O- | 1 | $-CH_2-$ | $-S-P(S)(O-1-C_3H_7)_2$ | $-S-P(S)(O-1-C_3H_7)_2$ | H | 0 | |
| 13. | " | 2 | $-CH_2CH_2-$ | -O- | 1 | $-CH_2-$ | $-S-P(S)$ (cyclic) | $-S-P(S)(O-1-C_3H_7)_2$ | H | 1 | $-CH_2-$ |
| 14. | ![HO-phenol with cyclohexyl and methyl] | 2 | $-CH_2CH_2-$ | -O- | 1 | $-CH_2-$ | H | (cyclic 5-membered S=P(O)(O)S) | H | 0 | ![phenol with t-Bu, ester linkage -O-C(=O)-CH_2CH_2-] |

-continued

Typical examples of compounds according to the invention corresponding to formula VII or VIII:

| No. | A | m | $-C_mH_{2m}-$ | X | n | $-C_nH_{2n}-$ | | | |
|---|---|---|---|---|---|---|---|---|---|
| 15. | HO—[2,6-substituted phenyl] | 1 | $-CH_2-$ | $-NH-$ | 1 | $-CH_2-$ | $-OH$ | H | H |
| 16. | " | 2 | $-CH_2CH_2-$ | $-O-$ | 1 | $-CH_2-$ | $-S-P(S)(O-C_9H_{19})_2$ $-S-P(S)(O-i-C_8H_{17})_2$ | H | H |
| 17. | " | 2 | $-CH_2CH_2-$ | $-O-$ | 1 | $-CH_2-$ | $-S-P(S)(O-i-C_4H_9)_2$ | H | $-CH_2-$ |
| 18. | HO—[substituted phenyl] | 2 | $-CH_2CH_2-$ | $-O-$ | 1 | $-CH_2-$ | H | $-S-P(S)(O-i-C_{13}H_{27})_2$ | H |

$$A-C_mH_{2m}-\overset{O}{\overset{\|}{C}}-X-C_nH_{2n}-\overset{R_7}{\overset{|}{C}}=\overset{R_8}{\overset{|}{C}}-C_rH_{2r}-Z \quad (VIII)$$

| No. | A | m | $-C_mH_{2m}-$ | X | n | $-C_nH_{2n}-$ | one of $R_7$ and $R_8$ is | and the other is | r | $-C_rH_{2r}-$ |
|---|---|---|---|---|---|---|---|---|---|---|
| 19. | HO—[2,6-substituted phenyl] | 1 | $-CH_2-$ | $-O-$ | 1 | $-CH_2-$ | H | $-S-P(S)(O-i-C_3H_7)_2$ | r | $-C_rH_{2r}-$ |
| 20. | " | 2 | $-CH_2CH_2-$ | $-O-$ | 1 | $-CH_2-$ | H | $-S-P(S)(O-1-C_8H_{17})_2$ | 0 | H |
| 21. | " | 2 | $-CH_2CH_2-$ | $-O-$ | 0 |  | H | $-S-P$ (cyclic phosphite structure) | 1 0 | $-CH_2-$ |

| No. | A | m | $-C_mH_{2m}-$ | X | n | $-C_nH_{2n}-$ | one of $R_7$ and $R_8$ is | and the other is | r | $-C_rH_{2r}-$ |
|---|---|---|---|---|---|---|---|---|---|---|
| 22. | HO—[2,6-substituted phenyl] | 2 | $-CH_2CH_2-$ | $-O-$ | 1 | $-CH_2-$ | H | H | 0 | $-C_rH_{2r}-$ |
| 23. | " | 2 | $-CH_2CH_2-$ | $-O-$ | 1 | $-CH_2-$ | a further C—C bond with $R_7$ or $R_8$ | a further C—C bond with $R_7$ or $R_8$ | 0 | H |

The compounds of the formula I are produced in a manner known per se, for example by esterification of a carboxylic acid, or of a reactive derivative, such as an acid chloride or lower alkyl ester of the formula IX

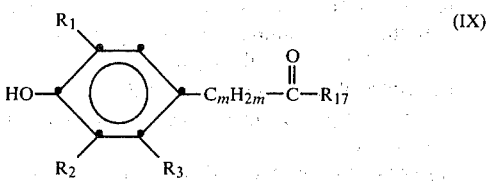

wherein $R_{17}$ is OH, Cl or $C_1$–$C_4$-alkoxy, and the remaining symbols have the meanings defined in the foregoing, with a hydroxyalkene, -epoxide or -alkyne of the formula X $$HO—(C_nH_{2n}—Y^*)_q—C_rH_{2r}—Z \qquad (X)$$

wherein $Y^*$ is a group

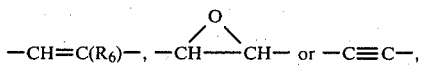

and the remaining symbols of the formula X and $R_6$ have the meanings already defined. To the compound of the formula XI obtained in this manner

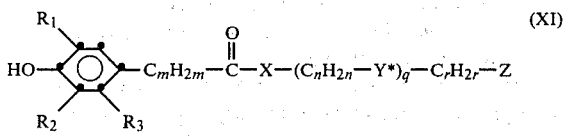

wherein the symbols have the meanings defined in the foregoing, there is optionally added a compound of the formula XII

wherein $R_9$ and $R_{10}$ have the meanings defined in the foregoing.

The addition can be performed in an inert solvent, or preferably without solvent, at temperatures of 0°–180° C., advantageously however without solvent at temperatures of 0°–180° C., preferably at 50°–150° C., and optionally in the presence of a radical initiator. Suitable solvents are optionally chlorinated aliphatic or aromatic hydrocarbons, such as special grades of petroleum spirit, or hexane, heptane, methylene chloride, 1,2-dichloroethane, benzene, chlorobenzene, dichlorobenzene, toluene or xylene; or ethers, such as diethyl ether, dioxane or tetrahydrofuran.

Radical initiators usable for the radically catalysed addition reaction are for example in particular: peroxy and azo compounds, or UV light. Customary peroxy compounds are hydrogen peroxide, di-t-butyl peroxide, cumene hydroperoxide or dibenzoyl peroxide. A suitable azo compound is especially α,α'-azodiisobutyric acid dinitrile.

If the dithiophosphoric acid-O,O-diester of the formula XII is reacted with an alkene of the formula XI wherein $Y^*$ is —CH=C($R_6$)—, and the remaining symbols have the meaning defined in the foregoing, there are formed compounds of the formula I in which Y is a group of the formula II. There is obtained, in addition to the compound wherein $R_4$ is hydrogen, and $R_5$ is the group of the formula IV, as a rule the isomeric compound in which $R_4$ is a group of the formula IV and $R_5$ is hydrogen. The separation of the two isomers is possible in a known manner. Generally, however the isomeric mixture is used for application as lubricant additives.

When the dithiophosphoric acid-O,O-diester of the formula XII is reacted with an epoxide of the formula XI in which

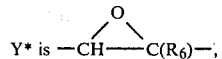

and the remaining symbols have the aforementioned meanings, there are formed compounds in which Y is a group of the formula II wherein one of the symbols $R_4$ and $R_5$ is hydroxyl, and the other is a group of the formula IV. In this case too, there is formed as a rule an isomeric mixture, which can if desired be separated.

If the dithiophosphoric acid-O,O-diester of the formula XII is reacted with an alkyne of the formula XI wherein $Y^*$ is —C≡C—, and the remaining symbols have the meanings defined in the foregoing, there are formed, on reaction of approximately one mol of the compound of the formula XII with approximately one mol of the compound of the formula XI, those representatives of the formula I in which Y is a group of the formula III, with one of the radicals $R_7$ and $R_8$ being hydrogen and the other a group of the formula IV. There are formed as above isomeric mixtures in this case. If approximately two mols of a compound of the formula XII are reacted with approximately one mol of the compound of the formula XI ($Y^*$: —C≡C—), there are obtained as product substances of the formula I wherein Y is a group of the formula II in which $R_4$ and $R_5$ are a group of the formula IV.

The dithiophosphates of the formula XII are known compounds and are readily obtainable commercially.

The novel compounds of the formula XI are both stabilisers for organic materials and lubricants, and valuable intermediates. This applies in particular to the novel compounds of the formula XI, such as 3-(3,5-di-tert-butyl-4-hydroxyphenyl)-propionic acid allyl ester and 3-(3,5-di-tert-butyl-4-hydroxyphenyl)-propionic acid propargyl ester.

The compounds of the formula I according to the invention are effective antioxidants for organic material. They are suitable for stabilising a great number of organic polymers. Examples of polymers of this kind are:

1. Polymers which are derived from mono- and diolefins, such as polyethylene, which can be crosslinked, polypropylene, polyisobutylene, polymethylbut-1-ene, polymethylpent-1-ene, polyisoprene and polybutadiene.

2. Mixtures of the homopolymers mentioned under 1, for example mixtures of polypropylene and polyethylene, of polypropylene and polybut-1-ene and of polypropylene and polyisobutylene.

3. Copolymers of the monomers on which the homopolymers mentioned under 1 are based, such as ethylene/propylene copolymers, ethylene/but-1-ene copolymers, as well as terpolymers of ethylene and propylene with a diene, for example hexadiene, dicyclopentadiene or ethylidene.

4. Acrylonitrile copolymers, for example butadiene/acrylonitrile/methylmethacrylate copolymers and ABS.

5. Polystyrene and copolymers thereof, such as SAN, IPS, ASA and EP-modified styrene copolymers.

6. Halogen-containing vinyl polymers.

7. Polyurethanes.

8. Polycarbonates.

9. Polyamides.

10. Polyesters.

The stabilisers can be optionally combined with other additives, such as with other antioxidants, lubricants, such as Ca-stearate, pigments, dyes, UV-absorbers, sterically hindered amines as light stabilisers, metal deactivators, talcum and other fillers.

The stabilisers according to the invention are in general used in amounts of 0.01 to 5 percent by weight, relative to the material to be stabilised, whereby the amount can vary depending on the substrate and mode of application. Preferred amounts are from 0.05 to 2 percent by weight, particularly from 0.1 to 1 percent by weight.

Some of the stabilisers according to the invention where Y is formula III can also be grafted onto the polymers (cp. in this respect German Offenlegungsschrift No. 2,509,654). The stabilisers for this application are used in amounts of 0.01 to 5 or 10%, typically in amounts of 0.25 to 3%, and especially 0.5 to 2%, relative to the weight of the polymer. There is moreover added with the grafting method a radical former. The weight ratio of stabiliser to radical former is 100:1 to 0.25:1.

Even in very small amounts, the compounds of the formula I are effective as high-pressure additives in lubricants. Thus, mineral and synthetic lubricating oils, and also mixtures thereof, which contain 0.001 to 5 percent by weight, preferably 0.02 to 3 percent by weight, relative to the lubricant, of a compound of the formula I display excellent high-pressure lubricating properties which are clearly manifested in greatly reduced wear phenomena on the parts in contact which have been lubricated. The lubricants which can be used are commonly known to those skilled in the art, and are described for example in "Schmiermittel Taschenbuch" ["Lubricants Handbook"] (Hüthig Verlag, Heidelberg, 1974).

The lubricating-oil formulation can additionally contain other additives which are added in order to improve certain basic oil properties, additives such as antioxidants, metal passivators, rust inhibitors, agents for improving the viscosity index, pour-point depressors, dispersants/detergents and other additives which protect against wear.

Examples of antioxidants are:

(a) alkylated and non-alkylated aromatic amines and mixtures thereof, for example: dioctyldiphenylamine, mono-t-octylphenyl-α- and -β-naphthylamines, phenothiazine, dioctylphenothiazine, phenyl-α-naphthylamine and N,N'-di-sec-butyl-p-phenylenediamine;

(b) sterically hindered phenols, for example 2,6-di-tert-butyl-p-cresol, 4,4'-bis-(2,6-diisopropylphenol), 2,4,6-triisopropylphenol, 2,2'-thio-bis-(4-methyl-6-tert-butylphenol), 4,4'-methylene-bis-(2,6-di-tert-butylphenol) and tetra-[methylene-3-(3,5-di-tert-butyl-4-hydroxyphenyl)-propionate]-methane;

(c) alkyl phosphites, aryl phosphites or aralkyl phosphites, for example: trinonyl phosphite, triphenyl phosphite and diphenyldecyl phosphite;

(d) esters of thiodipropionic acid or thiodiacetic acid, for example: dilauryl thiodipropionate or dioctyl thiodiacetate;

(e) salts of carbamic and dithiophosphoric acids, for example: antimony diamyldithiocarbamate and zinc diamyldithiophosphate; and (f) combinations of two or more antioxidants from the above, for example: an alkylated amine and a sterically hindered phenol.

Examples of metal passivators are:

(a) for copper, for example: benzotriazole, tetrahydrobenzotriazole, 2-mercaptobenzothiazole, 2,5-dimercaptothiadiazole, salicylidene-propylenediamine and salts of salicylaminoguanidine;

(b) for lead, for example: sebacic acid derivatives, quinizarine and propyl gallate; and (c) a combination of two or more of the above additives.

Examples of rust inhibitors are:

(a) organic acids and their esters, metal salts and anhydrides, for example: N-oleoyl-sarcosine, sorbitane monooleate, lead naphthenate and dodecenyl-succinic anhydride;

(b) nitrogen-containing compounds, for example:

I. primary, secondary or tertiary aliphatic or cycloaliphatic amines and amine salts of organic and inorganic acids, for example oil-soluble alkyl-ammonium carboxylates, and II. heterocyclic compounds, for example: substituted imidazolines and oxazolines;

(c) phosphorus-containing compounds, for example: amine salts of phosphoric acid partial esters;

(d) sulfur-containing compounds, for example: barium dinonylnaphthalene-sulfonates and calcium petroleum sulfonates; and (e) combinations of two or more of the above additives.

Examples of *agents which improve the viscosity index* are: polymethacrylates, vinylpyrrolidone/methacrylate copolymers, polybutenes, olefine copolymers and styrene/acrylate copolymers.

Examples of *pour-point depressors* are: polymethacrylates and alkylated naphthalene derivatives.

Examples of *dispersants/detergents* are: polybutenylsuccinic acid imides, polybutenylphosphonic acid derivatives and hyperbasic sulfonates and phenolates of magnesium, calcium and barium.

Examples of other *additives which provide protection against wear* are: compounds which contain sulfur and/or phosphorus and/or halogen, such as vegetable oils treated with sulfur, zinc dialkyldithiophosphates, tritolyl phosphates, chlorinated paraffins, alkyl disulfides and aryl disulfides.

The Examples which follow further illustrate the invention.

EXAMPLE 1

Isomeric mixture of the formula

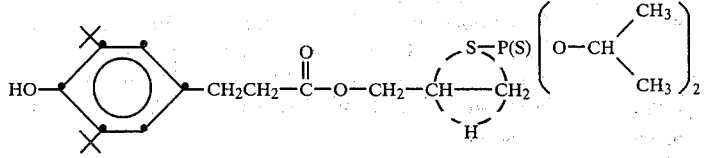

214 g (1 mol) of di-thiophosphoric acid-0,0-di-isopropyl ester are added under nitrogen to 318 g (1 mol) of 3,5-di-t-butyl-4-hydroxyphenyl-propionic acid allyl ester, and with the addition of all together 1 g of α,α'-azodiisobutyric acid dinitrile the mixture is heated for 15 hours at 110°–120° C., the catalyst being added in 5–10 portions spread over the entire reaction period. There is formed a slightly brownish viscous reaction product, which contains only a small amount of allyl ester. After all volatile by-products have been evaporated off in vacuo (2 KPa/80° C.), the title product can be used for the application according to the invention as a lubricant additive without further purification.

EXAMPLE 2

Isomeric mixture of the formula

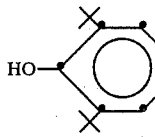

If the dithiophosphoric acid-0,0-di-isopropyl ester of Example 1 is replaced by 353 g (1 mol) of the corresponding 0,0-di-2-ethyl-n-hexyl ester, there is obtained using otherwise an analogous procedure, also without addition of a radical initiator, the title compound in the form of a brownish viscous oil.

EXAMPLE 3

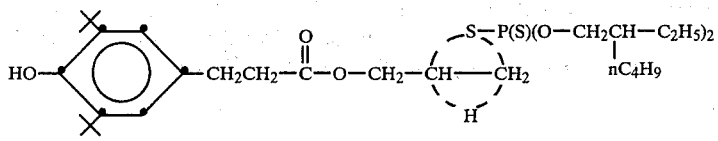

214 g (1 mol) of di-thiophosphoric acid-0,0-di-isopropyl ester are added under nitrogen to 158 g (0.5 mol) of 3,5-di-t-butyl-4-hydroxyphenylpropionic acid propargyl ester, and analogously to Example 1 the mixture is heated with all together 1 g of α,α'-azoisobutyric acid dinitrile for 16 hours at 110° C. with stirring. There is formed the title compound in the form of a slightly coloured oil which, according to the elementary analysis, contains two dithiophosphate radicals per mol. After removal of volatile fractions in vacuo, the substance can be used without further purification as a lubricant additive.

EXAMPLE 4

Isomeric mixture

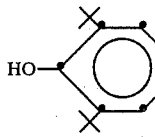

177 g (0.5 mol) of di-thiophosphoric acid-0,0-di-2-ethyl-n-hexyl ester are added at 20° C. under nitrogen in the course of 30 minutes, with stirring, to 167 g (0.5 mol) of 3,5-di-t-butyl-4-hydroxyphenylpropionic acid-2-epoxypropyl ester, the temperature rising in the process to about 50° C. The reaction mixture is stirred for a further 2 hours without any further supply of heat. The title compound obtained is an almost colourless viscous oil.

EXAMPLE 5

3-(3,5-Di-t-butyl-4-hydroxyphenyl)-propionic acid allyl ester 0.2 g of lithium amide and in the course of 5 hours 38 g of allyl alcohol are added at 150° C. under nitrogen to 146 g of 3-(3,5-di-t-butyl-4-hydroxyphenyl)-propionic acid methyl ester. After completion of the addition, stirring is maintained at 150° C. for a further 10 hours. The brownish reaction mixture is cooled to about 100° C., and 150 ml of toluene, 0.5 g of concentrated acetic acid and 10 g of "Celite Hyflow Supercel" (product of Johns Manville Corp., USA) are added. There is thus obtained, after filtration and then removal of the solvent in vacuo, the title compound in crystalline form, m.p. about 40° C.

EXAMPLE 6

3-(3,5-Di-t-butyl-4-hydroxyphenyl)-propionic acid propargyl ester

By replacing in Example 5 the allyl alcohol by propargyl alcohol, and lithium amide by Ti(IV)-butylate, there is obtained, using otherwise the analogous procedure, after about 25 hours' heating at 120°–130° C., the title compound as a colourless oily liquid, b.p.$_{0.02}$: 145°–146° C.

EXAMPLE 7

The following values were determined using the Shell four-ball apparatus (Tentative method IP 239/69, extreme pressure and wear lubricant test for oils and greases, four-ball machine).

(1) I.S.L.=Initial Seizure Load: that is the load under which the oil film breaks down within a duration of load application of 10 seconds.

(2) W.L.=Weld Load: that is the load under which the 4 balls weld together within 10 seconds.

(3) W.S.D.=Wear Scar Diameter in mm: that is the mean wear diameter with a loading of 70 kg or 40 kg for 1 hour.

Vitrea 41 (Shell trade name) was used as the base oil. Concentration of the stabiliser: 1 percent by weight.

TABLE 1

| Stabiliser | ISL (kg) | WL (kg) | WSD (mm) |
|---|---|---|---|
| none | about 60 | about 160 | about 2.4 |
| Example 1 | 140 | 250 | 0.4 |
| Example 2 | 100 | 200 | 0.3 |
| Example 3 | | | 0.4 |
| Example 5 | | | 0.6 |

EXAMPLE 8

Oil-oxidation test, standard version according to ASTM D 2272 (Rotary Bomb Oxidation Test)

An oil specimen of 50 ml of mineral oil, "Vitrea 41" (SHELL trade name), with the addition of 0.25 g of stabiliser is oxidised, in a glass vessel, together with 5 ml of distilled water and a polished, catalytically acting copper coil, which has been washed with petroleum ether, in an oxygen atmosphere. The glass vessel is in a stainless-steel bomb fitted with a pressure gauge. The bomb rotates axially at 100 r.p.m., at an angle of 30° with the horizontal, in an oil bath at 150° C. Before heating commences, the oxygen pressure is initially about 6 bars; it increases at 150° C. to nearly 14 bars and then remains constant until oxidation occurs. The test is terminated with a drop in pressure of 1.7 bars, and the time until that occurs is recorded in minutes.

TABLE 2

| Stabiliser | Minutes until drop in pressure of 1.7 bars occurs |
|---|---|
| none | 16 |
| Example 1 | 162 |
| Example 2 | 70 |
| Example 3 | 158 |
| Example 5 | 102 |

EXAMPLE 9

Oil-oxidation test according to IP 280, "CIGRE"

Modified version with soluble Cu and Fe catalyst.

Conditions: Introduction of oxygen for 4 hours at 150° C. (4 liters of O$_2$/h).

Determination of the acid number after end of test; table value: mg KOH consumption per gram of test oil.

Stabiliser concentration: 0.5 percent by weight.

Test oil: mineral oil "Vitrea 41" (SHELL trade name).

TABLE 3

| Stabiliser | mg KOH/g |
|---|---|
| none | 3.6 |
| Example 1 | 1.25 |
| Example 2 | 0.7 |
| Example 3 | 0.9 |

What is claimed is:

1. A compound of formula I

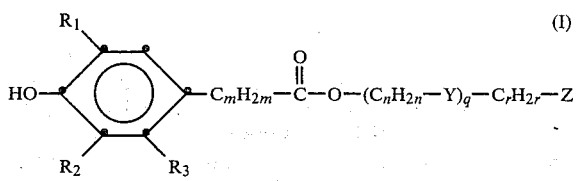

wherein $R_1$ and $R_2$ independently of one another are each $C_1$–$C_{12}$-alkyl, or they are phenyl, $C_7$–$C_9$-aralkyl or $C_5$–$C_7$-cycloalkyl, each of which is unsubstituted or substituted by 1 to 3 alkyl groups having a total of 1 to 12 C atoms, and $R_2$ in addition is hydrogen or chlorine, $R_3$ is hydrogen or methyl, m is nought, 1, 2, 3 or 4, n and r independently of one another are each an integer from nought to 20 inclusive, q is 1, 2 or 3, with the proviso that (n·q)+r is an integer from nought to 24 inclusive, and Y is a group of the formula II or III

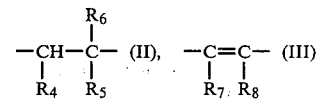

in which $R_4$ and $R_5$ are each hydrogen or hydroxyl, and at least one of the radicals $R_4$ and $R_5$ is a group of the formula IV

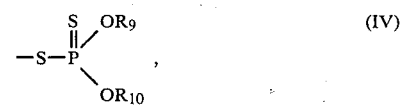

$R_6$ is hydrogen or methyl, one of the radicals $R_7$ and $R_8$ is hydrogen, and the other is a group of the formula IV, wherein $R_9$ and $R_{10}$ independently of one another are each $C_1$–$C_{30}$-alkyl or $C_2$–$C_{10}$-alkoxyalkyl, or they are phenyl, $C_7$–$C_9$-aralkyl or $C_5$–$C_7$-cycloalkyl, each of which is unsubstituted or substituted by 1 to 3 alkyl groups having a total of 1 to 12 C atoms, or $R_9$ and $R_{10}$ together are a group of the formula V

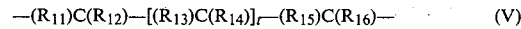

wherein t is nought or 1, and $R_{11}$, $R_{12}$, $R_{13}$, $R_{14}$, $R_{15}$ and $R_{16}$ independently of one another are each hydrogen or methyl, and Z is hydrogen or a group of the formula VI

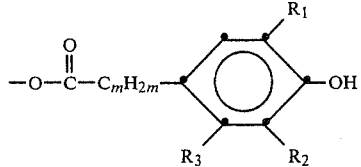 (VI)

in which the symbols $R_1$, $R_2$, $-R_3$ and m have the meanings defined above.

2. A compound according to claim 15 of the formula I, wherein $R_1$ and $R_2$ independently of one another are each $C_1$–$C_8$-alkyl, with $R_2$ in addition being hydrogen, $R_3$ is hydrogen or methyl, m is 1 or 2, n and r independently of one another are each an integer from nought to 8 inclusive, q is 1, with the proviso that $(n \cdot q) + r$ is an integer from nought to 16 inclusive, Y is a group of the formula II or III wherein $R_4$ and $R_5$ are each hydrogen or hydroxyl, and at least one of the radicals $R_4$ and $R_5$ from nought to 6 inclusive, r is nought or 1, q is 1, Y is a group of the formula II or III, in which one of the substituents $R_4$ and $R_5$ is hydrogen and the other is a group of the formula IV, wherein $R_9$ and $R_{10}$ have the meanings given in claim 2.

4. A compound according to claim 3 of the formula I wherein n is 1, r is nought, and q is 1.

5. A compound according to claim 1 of the formula I wherein Y is a group of the formula II.

6. A compound according to claim 1 of the formula I wherein m is 1 or 2.

7. A compound according to claim 1 of the formula I wherein Z is hydrogen.

8. A compound according to claim 1 of the formula I wherein q is 1.

9. A compound according to claim 8 of the formula I wherein r is nought.

10. A composition consisting essentially of a major proportion of the isomeric mixture of compounds according to claim 1 of the formula

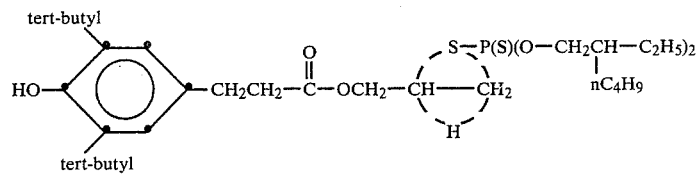

is a group of the formula IV, $R_6$ is hydrogen, one of the radicals $R_7$ and $R_8$ is hydrogen, and the other is a group of the formula IV, wherein $R_9$ and $R_{10}$ independently of one another are each $C_1$–$C_{22}$-alkyl, or $R_9$ and $R_{10}$ together are a group of the formula V, wherein the symbols t and $R_{11}$ to $R_{16}$ have the meanings given in claim 1, and Z is hydrogen.

3. A compound according to claim 2 of the formula I, wherein $R_1$ is t-butyl, t-amyl or 1,1,3,3-tetramethylbutyl, $R_2$ is $C_1$–$C_8$-alkyl, $R_3$ is hydrogen, n is an integer and a minor proportion of allyl 3-(3,5-di-tert-butyl-4-hydroxyphenyl)propionate.

11. Organic material containing an effective stabilizing amount of a compound of the formula I according to claim 1.

12. A lubricant containing an effective stabilizing amount of a compound of the formula I according to claim 1.

* * * * *